US008535267B2

(12) United States Patent
Caizza

(10) Patent No.: US 8,535,267 B2
(45) Date of Patent: Sep. 17, 2013

(54) RETRACTABLE SYRINGE WITH SEGMENTED RETAINING LEDGE

(75) Inventor: Richard Caizza, Vernon, NJ (US)

(73) Assignee: Midland Medical Devices Holdings, LLC, Midland, TX (US)

( * ) Notice: Subject to any disclaimer, the term of this patent is extended or adjusted under 35 U.S.C. 154(b) by 0 days.

(21) Appl. No.: 13/413,572

(22) Filed: Mar. 6, 2012

(65) Prior Publication Data
US 2012/0232482 A1 Sep. 13, 2012

Related U.S. Application Data

(60) Provisional application No. 61/449,981, filed on Mar. 7, 2011.

(51) Int. Cl.
*A61M 37/00* (2006.01)

(52) U.S. Cl.
USPC .......................................... 604/110

(58) Field of Classification Search
USPC .......................................... 604/110
See application file for complete search history.

(56) References Cited

U.S. PATENT DOCUMENTS

| 5,171,300 | A | | 12/1992 | Blake, III et al. | |
|---|---|---|---|---|---|
| 5,407,436 | A | * | 4/1995 | Toft et al. | 604/195 |
| 5,935,104 | A | * | 8/1999 | Janek et al. | 604/110 |
| 6,706,015 | B2 | | 3/2004 | Bang | |
| 7,803,132 | B2 | * | 9/2010 | Janek et al. | 604/110 |
| 8,034,025 | B1 | * | 10/2011 | Chang | 604/110 |
| 2003/0212366 | A1 | * | 11/2003 | Bang | 604/196 |
| 2006/0189935 | A1 | * | 8/2006 | Janek et al. | 604/110 |
| 2007/0060885 | A1 | * | 3/2007 | Wu | 604/110 |
| 2008/0045899 | A1 | * | 2/2008 | Wu | 604/110 |
| 2011/0092902 | A1 | * | 4/2011 | Kiehne | 604/110 |
| 2012/0232480 | A1 | * | 9/2012 | Caizza | 604/110 |
| 2012/0232481 | A1 | * | 9/2012 | Caizza | 604/110 |
| 2012/0232483 | A1 | * | 9/2012 | Caizza et al. | 604/110 |

OTHER PUBLICATIONS

International Search Report and Written Opinion—PCT/us2012/027924.

* cited by examiner

*Primary Examiner* — Aarti B Berdichevsky
(74) *Attorney, Agent, or Firm* — Robert C. Klinger

(57) ABSTRACT

A retractable needle syringe having a segmented retaining ledge at the distal end of the syringe barrel. The retaining ledge has uniformly spaced members configured to enable the retaining ring to break from the needle stem with a reduced plunger engagement force, which provides an improved tactile feeling of the syringe plunger and comfort of use. The segmented retaining ledge also makes it easier to install the needle stem and retaining ring in the barrel distal end, such that it snaps into place therepast with less axial force.

9 Claims, 5 Drawing Sheets

RETRACTABLE SYRINGE WITH SEGMENTED RETAINING LEDGE

CROSS REFERENCE TO RELATED APPLICATIONS

This application claims priority of U.S. Provisional Patent Application Ser. No. 61/449,981 entitled Retractable Syringe with Segmented Retaining Ledge, filed Mar. 7, 2011, the teachings of which are incorporated herein.

BACKGROUND OF THE INVENTION

The present invention is directed to safety syringes, and particularly syringes with retractable needles configured to retract after use and prevent re-use and unintended sticking. Retractable syringes are known in the art, which typically include a needle configured to automatically retract into a syringe barrel after delivery of a medicant into a patient. In some designs, a needle stem including a separable or breakable retaining ring thereabout is installed through a barrel proximal end and secured in the barrel distal end. The needle stem may be fixedly secured or selectively secured to a needle. Conventional mechanisms that secure the needle stem and retaining ring in place define a required axial plunger force required to selectively break the needle stem from the retaining ring after final use to allow automatic retraction of the spring biased needle.

There is desired a retractable syringe configured to enable the retaining ring to break from the needle stem with a reduced plunger engagement force, which provides an improved tactile feeling of the syringe plunger and comfort of use. There is also desired a retractable syringe configured to make it easier to install the needle stem and retaining ring in the barrel distal end, such that it can snap into place therepast with less axial force.

SUMMARY OF THE INVENTION

The present invention achieves technical advantages as a retractable needle syringe having a segmented retaining ledge at the distal end of the syringe barrel interior wall. The segmented retaining ledge is defined by a plurality of spaced raised dimples, notches or detents in the ledge to provide several features. The segmented retaining ledge locates the needle stem and retaining ring in the interior of the barrel and resists movement in the proximal direction due to the energized spring while enables the retaining ring to break from the needle stem with a reduced plunger engagement force, which provides an improved tactile feeling of the syringe plunger and comfort of use. The segmented ledge also makes it easier to install the needle stem and retaining ring in the barrel distal end, such that it snaps into place therepast with less axial force.

DETAILED DESCRIPTION OF A PREFERRED EMBODIMENT

Figure 1:
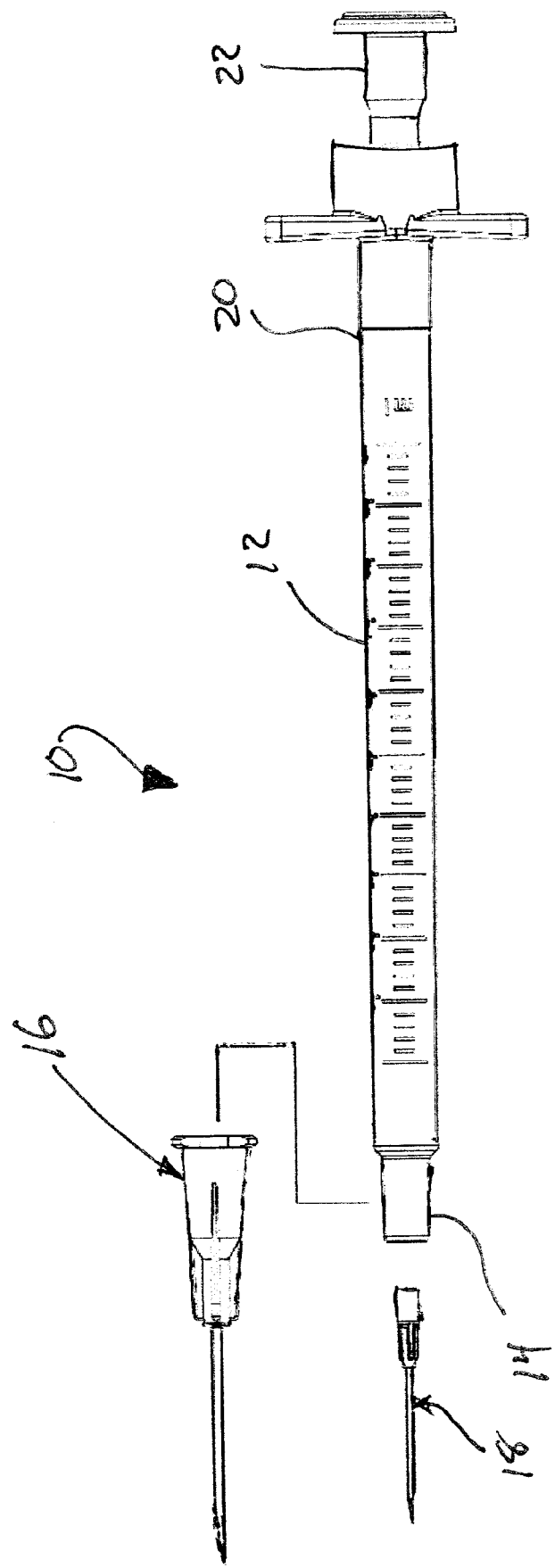
FIG. 1 shows an exploded view of a retractable syringe having a conical frustum tip, as well as an interchangeable needle and hub forming a needle assembly configured to extend through the conical frustum tip.

Referring to FIG. 1 there is shown a retractable needle syringe 10 having a syringe barrel 12 with a distal end 14 configured as a conical frustum tip. The conical frustum tip 14 is configured to attach to female Luer compatible devices including a filling needle & Luer hub 16 as shown, collectively referred to as a luer filling needle, as well as delivery tubes and the like. The syringe 10 is also shown to include a selectively attachable, interchangeable needle assembly 18 including a needle and threaded needle hub, allowing needles of different sizes and lengths to be interchanged with the syringe 10. Needle assembly 18 has radially extending ribs and is configured to be threadably coupled to a threaded needle stem 24 within the distal end of the conical frustum tip 14, as shown in the FIG. 2 as will be described shortly. Syringe 10 also includes a syringe proximal end 20 and a plunger 22 slidable therein from the proximal end, the plunger 22 configured to both aspirate a fluids through the Luer filling needle/hub 16, and also dispense the medicant upon compression. The plunger 22 is also configured to aspirate a fluid through the needle assembly 18 if desired. The filling needle/hub 16 may be desired as it is a common inexpensive needle that can also speed up the drawing process, and also prevents the possible unintentional retraction of the needle assembly 18 during insertion into the medicant vial or during the handling of the syringe 10 when drawing the medicant. Moreover, the conical frustum tip 14 advantageously allows the syringe 10 to be conveniently prefilled with medicant at one place and capped, then transported to a patient with or without needle assembly 18 as desired. This design is a significant advantage for many healthcare providers involved in the processing and handling of syringes until ultimate delivery of the medicant to a patient.

Figure 2:
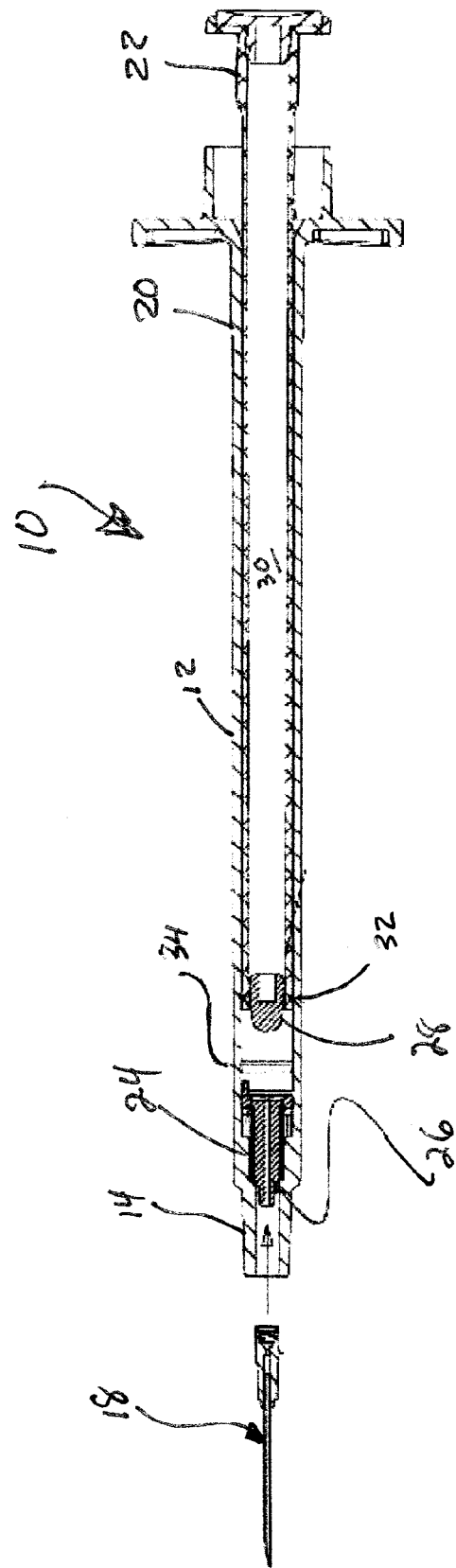
FIG. 2 shows a longitudinal cross sectional view of the syringe of FIG. 1 depicting a needle stem positioned in the syringe distal end and configured to receive the interchangeable needle assembly disposed through the conical frustum tip.

Referring to FIG. 2, there is shown a longitudinal cross sectional view of syringe 10 of FIG. 1, detailing the needle stem 24 having a threaded distal end 26 configured to receive the needle assembly 18. Notably, the needle stem 24 is positioned within the distal end of the conical frustum tip 14 and is advantageously protected from axial forces which could inadvertently being contacted and creating an unintended retraction of spring biased needle stem 24, such as when the needle assembly is secured to needle stem. Also shown is the plunger 22 having a plug 28 at a distal end thereof, which plug is in sealing arrangement with a cavity 30 of plunger 22 prior to retraction of needle assembly 18 therein, and which plug is dislodged into the cavity by the needle stem 24 that retracts with needle assembly 18 after an injection. The distal end of plunger 22 proximate the plug 28 has an integral seal 32 extending annularly thereabout. The interior surface of the syringe includes a plurality of annular detents 34 configured for positioning the seal 32 in a rested position, before the distal end of plunger 22 axially engages a protrusion 38 of an annular ring 36 coupled to the needle stem 24 by a breakable membrane, as more fully described in Applicant's U.S. Pat. No. 7,803,132 B1, the teaching of which are included herein by reference.

Figure 3:
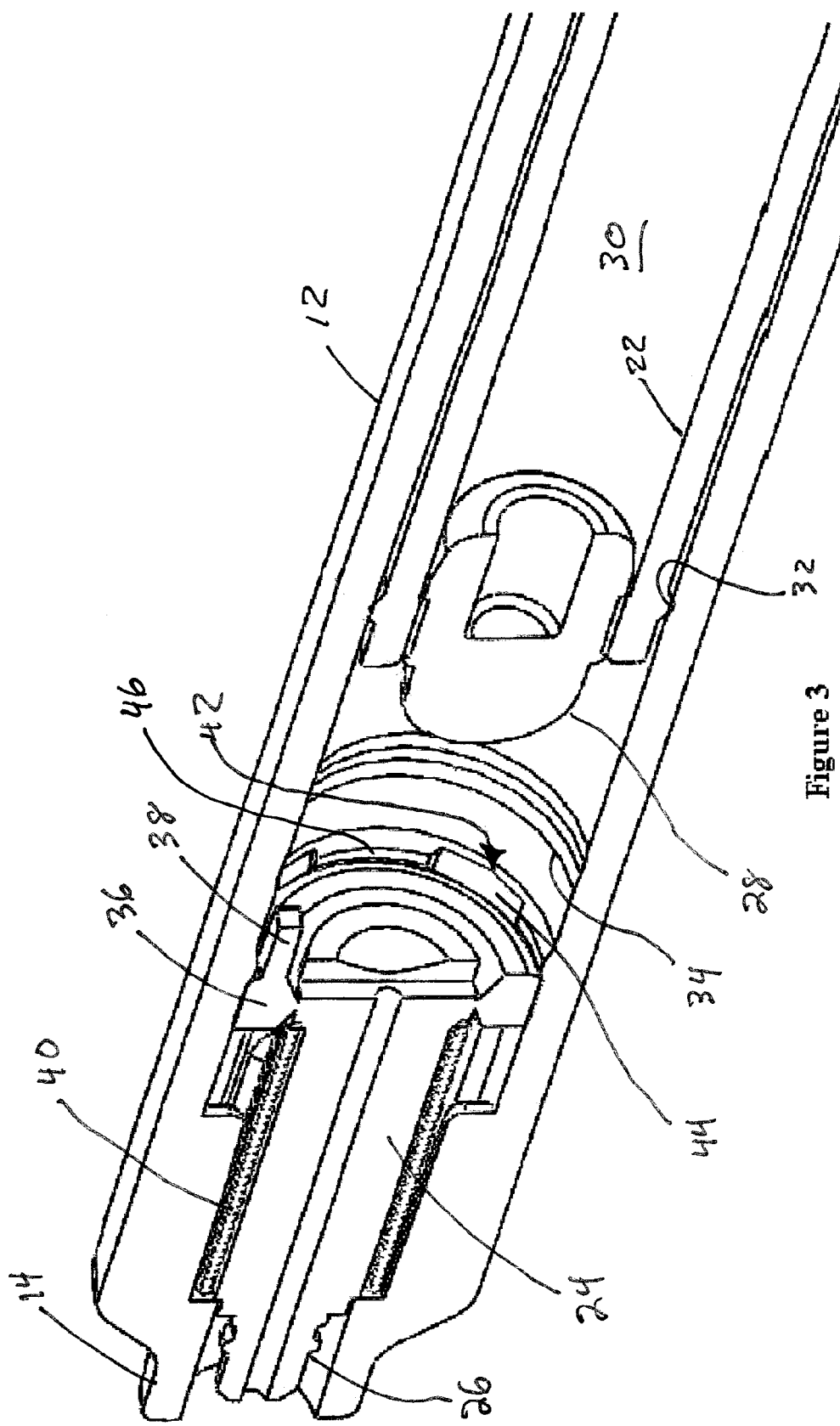
FIG. 3 shows an enlarged sectional view of the syringe distal end illustrating the needle stem having a threaded distal end configured to receive needles of various sizes through the conical frustum tip.

FIG. 3 depicts an enlarged cross sectional view of the needle stem 24, including the threaded needle distal end 26, positioned within the conical frustum tip 14, and coupled to the retaining ring 36 with protrusion 38 by the breakable membrane. Also shown is a spring 40 configured to retract the needle assembly 18 in response to the plunger 22 engaging the protrusion 38 after delivering the medicant to create a progressive separation of the retaining ring 36 from the needle stem 24 and the retraction of needle stem 24 into the plunger cavity 30. The annular detents 34 configured to seat position seal 32 are also shown.

This FIG. 3 also shows the interior surface of the barrel 12 including an annular retaining ledge generally shown at 42 configured to retain the needle stem 24 distally thereof such that the needle stem 24 is securely seated in the syringe barrel distal end, including during attachment of needle assembly 18, and until a complete retraction of the needle stem 24 and needle assembly 18 into cavity 30. Notably, the retaining ledge 42 is segmented, and is defined by segments of raised protrusions 44 extending from the interior barrel wall with notches or detents 46 defined between the protrusions 44 to provide several features. The segmented retaining ledge 42 enables reduced activation force required by the plunger to separate and break the retaining ring 36 from the needle stem 24, which provides an improved tactile feeling of the seal 32 and comfort of use. The segmented ledge 42 also makes it easier to install the needle stem 24 and retaining ring 36 in the barrel distal end, such that it snaps into place therepast with less axial force.

Figure 4:
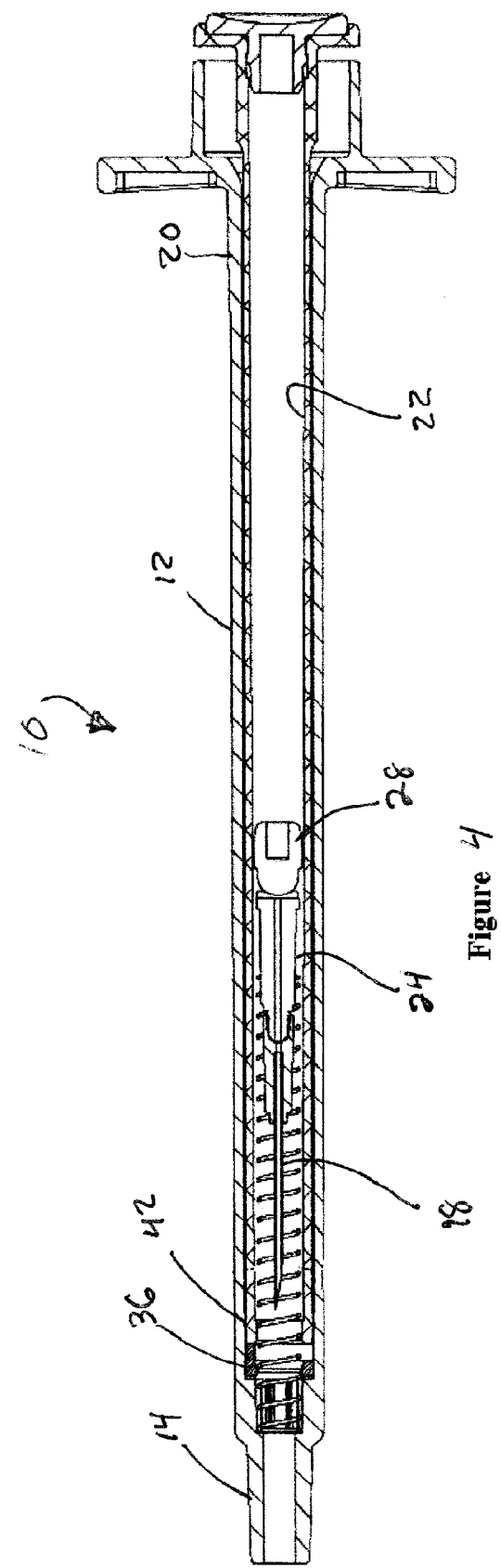
FIG. 4 shows a longitudinal cross sectional view of the syringe of FIG. 1 depicting the needle assembly after retraction into the syringe barrel.

FIG. 4 depicts the needle stem 24 and needle assembly 18 after retraction into the plunger cavity 30.

Figure 5:
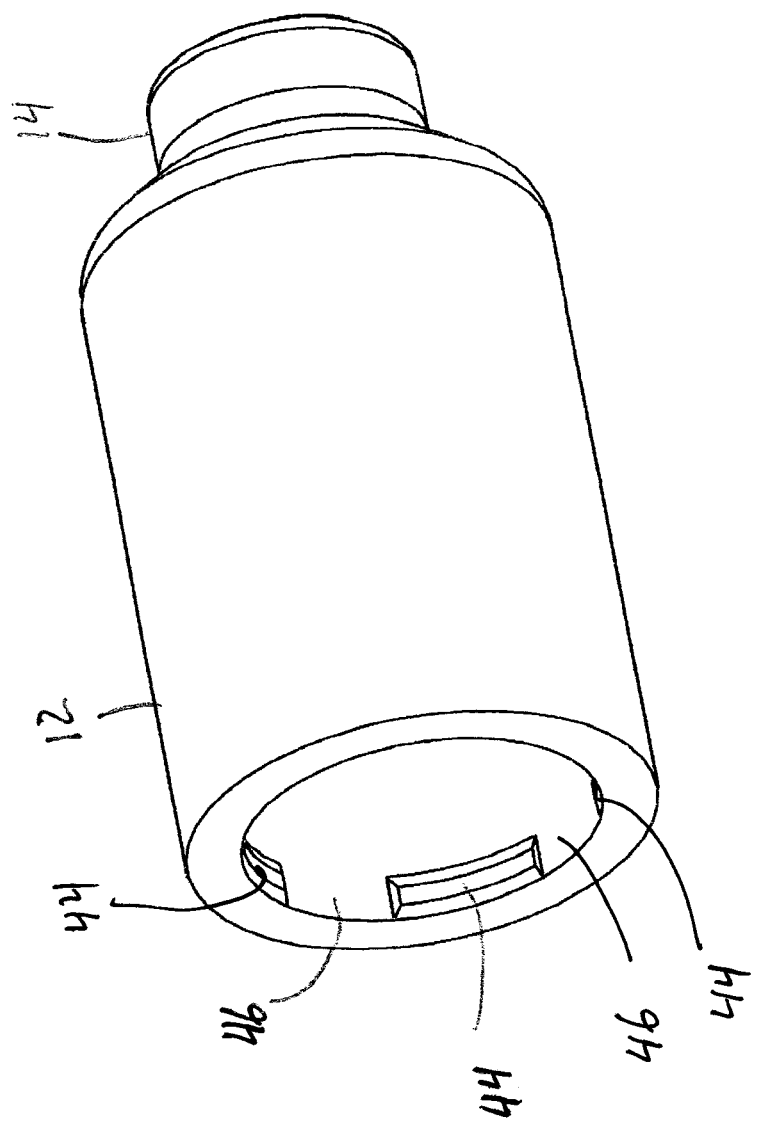
FIG. 5 shows a cross section of the syringe barrel just distal of the segmented retaining ledge shown in FIG. 3.

FIG. 5 depicts a cross section of the syringe barrel distal end taken proximate the segmented retaining ledge 42.

While the invention has been described in detail and with reference to a specific embodiment thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

I claim:

1. A syringe, comprising:
   a barrel having a proximal end and a distal end, and an interior surface defining a cavity configured as a fluid transfer device
   a plunger disposed in the barrel and configured to advance toward the barrel distal and proximal ends;
   a needle stem disposed in the barrel distal end;
   a needle assembly selectively coupled to the needle stem and configured to deliver a fluid upon advancement of the plunger toward the barrel distal end; and
   wherein the barrel interior surface comprises a segmented retaining ledge at the barrel distal end configured to secure the needle stem distal of the segmented retaining ledge, wherein the segmented retaining ledge comprises a plurality of members extending inwardly from the barrel interior surface with a space defined between each of the members, wherein the needle stem includes a retaining ring disposed annularly thereabout, wherein the segmented retaining ledge is configured to reduce an engagement force of the plunger necessary to separate the retaining ring from the needle stem.

2. The syringe as specified in claim 1 wherein the segmented retaining ledge extends annularly about the barrel cavity.

3. The syringe as specified in claim 1 wherein the members are uniformly spaced from one another.

4. The syringe as specified in claim 1 wherein the retaining ring is configured to be broken from the needle stem, wherein the segmented retaining ledge is configured to reduce an engagement force of the plunger necessary to break the retaining ring from the needle stem.

5. The syringe as specified in claim 1 wherein the needle stem and the needle assembly are configured to automatically retract past the segmented retaining ledge and within the barrel upon delivery of the fluid from the barrel.

6. The syringe as specified in claim 5 wherein the needle stem is spring biased toward the barrel proximal end.

7. A syringe, comprising:
   a barrel having a proximal end and a distal end, and an interior surface defining a cavity configured as a fluid transfer device a plunger disposed in the barrel and configured to advance toward the barrel distal and proximal ends;
   a needle stem disposed in the barrel distal end;
   a needle assembly selectively coupled to the needle stem and configured to deliver a fluid upon advancement of the plunger toward the barrel distal end; and
   wherein the barrel interior surface comprises a segmented retaining ledge at the barrel distal end configured to secure the needle stem distal of the segmented retaining ledge, wherein the segmented retaining ledge comprises a plurality of members extending inwardly from the barrel interior surface with a space defined between each of the members, wherein the needle stem includes a retaining ring disposed annularly thereabout, wherein the segmented retaining ledge is configured to reduce an axial force required to advance the retaining ring distally thereover.

8. The syringe as specified in claim 7 wherein the segmented retaining ledge has rounded surfaces configured to engage the needle stem as it is advanced distally thereover during installation into the barrel distal end.

9. A syringe, comprising:
   a barrel having a proximal end and a distal end, and an interior surface defining a cavity configured as a fluid transfer device a plunger disposed in the barrel and configured to advance toward the barrel distal and proximal ends;
   a needle stem disposed in the barrel distal end;
   a needle assembly selectively coupled to the needle stem and configured to deliver a fluid upon advancement of the plunger toward the barrel distal end; and
   wherein the barrel interior surface comprises a segmented retaining ledge at the barrel distal end configured to secure the needle stem distal of the segmented retaining ledge, wherein the segmented retaining ledge comprises a plurality of members extending inwardly from the barrel interior surface with a space defined between each of the members, wherein the barrel has a space distal of the segmented retaining ledge, wherein the needle stem is configured to snap distal of the segmented retaining ledge and seat in the space.

* * * * *